United States Patent [19]

Gamble et al.

[11] Patent Number: 4,728,575
[45] Date of Patent: Mar. 1, 1988

[54] CONTRAST AGENTS FOR NMR IMAGING

[75] Inventors: Ronald C. Gamble, Altadena; Paul G. Schmidt, San Marino, both of Calif.

[73] Assignee: Vestar, Inc., Pasadena, Calif.

[21] Appl. No.: 720,954

[22] Filed: Apr. 10, 1985

Related U.S. Application Data

[63] Continuation-in-part of Ser. No. 604,721, Apr. 27, 1984, abandoned.

[51] Int. Cl.$^4$ .............................................. B32B 5/16
[52] U.S. Cl. .................................. 428/402.2; 264/4.3; 264/4.6; 424/1.1; 324/308; 128/660
[58] Field of Search ....................... 128/653, 654, 660; 324/308; 428/402.2; 260/403; 264/4.3, 4.6; 424/38, 182, 1.1, 19; 436/829

[56] References Cited

U.S. PATENT DOCUMENTS

| | | |
|---|---|---|
| 3,850,578 | 11/1974 | McConnell . |
| 4,192,859 | 3/1980 | Mackaness . |
| 4,301,054 | 11/1981 | Buirley et al. .................... 428/402.2 |
| 4,320,121 | 3/1982 | Sears ................................ 428/402.2 |
| 4,342,739 | 8/1982 | Kakimi et al. ................... 428/402.2 |
| 4,442,834 | 4/1984 | Rasor et al. .......................... 128/660 |
| 4,452,747 | 6/1984 | Gersonde et al. ................ 428/402.2 |
| 4,466,442 | 8/1984 | Hilmann et al. ..................... 128/653 |
| 4,485,045 | 11/1984 | Regen ............................... 428/402.2 |
| 4,485,054 | 11/1984 | Mezei et al. ...................... 428/402.2 |

FOREIGN PATENT DOCUMENTS

| | | |
|---|---|---|
| 898708 | 5/1984 | Belgium . |
| 0055576 | 7/1982 | European Pat. Off. . |
| 0071564 | 2/1983 | European Pat. Off. . |
| 0133603 | 2/1985 | European Pat. Off. . |
| 0136812 | 4/1985 | European Pat. Off. . |

OTHER PUBLICATIONS

J. Koutcher, *Contrast Agents and Spectroscopic Probes in NMR*, vol. 25, No. 4, Adjunctive Medical Knowledge, 506–513.

Mendonca Dias et al., *The Use of Paramagnetic Contrast Agents in NMR Imaging*, Absts. Soc. Mag. Res. Med., 1982, pp. 103–106.

Brady et al., *Proton Nuclear Magnetic Resonance Imaging of Regionally Ischemic Canine Hearts: Effects of Paramagnetic Proton Signal Enhancement*, Radiology, 1982, 144, pp. 343–347.

Brasch et al., *Evaluation of Nitroxide Stable Free Radicals for Contrast Enhancement in NMR Imaging*, Absts. Soc. Mag. Res. Med., 1982, pp. 25–26.

Brasch, *Work in Progress: Methods of Contrast Enhancement for NMR Imaging and Potential Applications*, Radiology, 1983, 147, pp. 781–788.

Grossman et al., *Gadolinium Enhanced NMR Images of Experimental Brain Abscess*, J. Comput. Asst. Tomogr., 1984, 8, pp. 204–207.

Andrasko et al., *NMR Study of Rapid Water Diffusion Across Lipid Bilayers in Dipalymitoyl Lecithin Vesicles*, Biochem. and Biophys. Res. Comm. 1974, 60 pp. 813–819.

Proffitt et al., *Liposomal Blockade of the Reticuloendothelial System: Improved Tumor Imaging with Small Unilamellar Vesicles* Science, 1983 220, pp. 502–505.

Proffitt et al., *Tumor–Imaging Potential of Liposomes Loaded with In–111–NTA: Biodistribution in Mice* Journal of Nuclear Medicine, 1983, 24, pp. 45–51.

(List continued on next page.)

*Primary Examiner*—Donald P. Walsh
*Assistant Examiner*—T. J. Wallen
*Attorney, Agent, or Firm*—Lyon & Lyon

[57] ABSTRACT

An agent for contrast enhancement in nuclear magnetic resonance imaging is disclosed. Micellular particles such as phospholipid vesicles are associated with or enclose a paramagnetic material. The particles may be formulated with an agent, such as cholestrol, to promote vesicle stability and water exchange across the vesicle bilayer. The vesicles may or may not have antibodies or other cell recognition targeting agents attached to the surface to provide specific targeting. The vesicles provide enhanced target specificity, reduced burden of toxic contrast material and amplified contrast enhancement.

25 Claims, 6 Drawing Figures

OTHER PUBLICATIONS

Brady, et al., *Selective Decrease in the Relaxation Times of Infrared Myocardium with the Use of a Manganese-Labelled Monoclonal Antibody*, Soc. Magn. Res. Med., Works in Progress, Second Annual Meeting, 1983, p. 10.

Farrar, T. C., Becker, E. D., *Pulse and Fourier Transform NMR*, 1971, Academic Press, New York.

Carr, H. Y., Purcell, E. H., *Effects of Diffusion on Free Precession in NMR Experiments*, Phys. Rev., 1954, 94, pp. 630-638.

Meiboom and Gill Meiboom S., Gill D., *Modified Spin-Echo Method for Measuring Nuclear Relaxation Times*, Rev. Sci. Instrum., 1958 29, pp. 688-691.

Martin et al., *Immunospecific Targeting of Liposomes to Cells*, Biochemistry, 1981, 20, pp. 4229-4238.

Hui et al., *Monoclonal Antibodies to a Synthetic Fibrin-Like Peptide Bind to Human Fibrin but not Fibrinogen*, Science, 1983, 222, pp. 1129-1131.

Mauk, et al., *Targeting of Lipid Vesicles: Specificity of Carbohydrate Receptor Analogues for Leukocytes in Mice*, Proc. Nat'l Acad. Sci., U.S.A. 77, 4430-4434 1980.

Mauk, et al., *Vesicle Targeting: Timed Release and Specificity for Leukocytes in Mice by Subcutaneous Injection*, Science 207 309-311 (1980).

Gadian et al., *Gadolinium—DPTA as a Contrast Agent in MR Imaging-Theoretical Projections and Practical Observations*, J. Comput. Asst. Tomogr., 1985, 9, pp. 242-251.

Parasassi et al., *Paramagnetic Ions Trapped in Phosphidipid Vesicles as Contrast Agents in NMR Imaging*, Inorganica Chimica Acta, 1985, 106, 135-139.

Caride et al., *Relaxation Enhancement Using Liposomes Carrying Paramagnetic Species*, Magnetic Resonance Imaging, 1984, 2, 107-112.

CONTRAST AGENTS FOR NMR IMAGING

RELATED APPLICATION

This application is a continuation-in-part of pending U.S. application, Ser. No. 604,721, filed April 27, 1984, now abandoned entitled "Contrast Agents For NMR Imaging."

BACKGROUND OF THE INVENTION

1. Field of the Invention

The invention described herein relates to enhanced contrast in nuclear magnetic resonance (NMR) imaging through the use of a paramagnetic material in association with micellular particles such as phospholipid vesicles.

2. Description of Prior Art

NMR imaging of humans is fast becoming a major diagnostic tool. Resolution is now on a par with X-ray CT imaging, but the key advantage of NMR is its ability to discriminate between tissue types (contrast) on the basis of differing NMR relaxation times, $T_1$ and $T_2$. Because nuclear relaxation times can be strongly affected by paramagnetic ions such as Mn(II) and Gd(III) or stable free radicals, these materials have been explored to determine their ability to provide further contrast, specifically to test whether they alter water proton $T_1$ and $T_2$ values in excised animal organs and in live animals; see, for example, Mendonca Dias et al, *The Use of Paramagnetic Contrast Agents in NMR Imaging*, Absts. Soc. Mag. Res. Med., 1982, pages 103, 104; Brady et al, *Proton Nuclear Magnetic Resonance Imaging of Regionally Ischemic Canine Hearts: effects of Paramagnetic Proton Signal Enhancement*, Radiology, 1982, 144, pages 343–347; and Brasch et al, *Evaluation of Nitroxide Stable Free Radicals for Contrast Enhancement in NMR Imaging*, Absts. Soc. Mag. Res. Med., 1982, pages 25, 26; Brasch, *Work in Progress: Methods of Contrast Enhancement for NMR Imaging and Potential Applications*, Radiology, 1983, 147, p. 781–788; and Grossman et al, *Gadolinium Enhanced NMR Images of experimental Brain Abscess*, J. Comput. Asst. Tomogr., 1984, 8, p. 204–207. Results reported show that contrast is enhanced by a variety of paramagnetic agents.

However, useful compounds, due to the nature of the candidate paramagnetic materials, may be toxic at the concentrations required for optimal effect, and finding contrast agents for which the toxicity is low enough to make possible their eventual use in medical diagnosis is regarded as the most serious and difficult problem in the field, Mendonca Dias et al, *The Use of Paramagnetic Contrast Agents in NMR Imaging*, Absts. Soc. Mag. Res. Med., 1982, pages 105, 106. The invention described herein is thus designed to reduce toxicity and increase the utility of NMR contrast agents by associating a paramagnetic material with a micellular particle having properties tailored to the unique demands of NMR imaging.

Another significant problem which must be addressed is that the maximum tissue volume occupied by micelles such as vesicles generally does not exceed about 0.1%, which means that the micelle must be capable of affecting an image with a very small volume percentage. In this regard, however, paramagnetic NMR contrast agents differ fundamentally from contrast agents used as X-ray absorbers, gamma ray emitters or the like in other imaging modalities in which the signal or attenuation is simply proportional to the number per unit volume, no matter how they are chemically bound or entrapped. In NMR, the agent (ion or stable free radical) acts to increase the relaxation rate of bulk water protons surrounding the free electron spin. The phenomenon depends on rapid exchange of water on and off an ion or rapid diffusion of water past an organic free radical. In such case, the net relaxation rate is a weighted average for free and bound water.

Encapsulation of the paramagnetic material within a phospholipid vesicle, as in one preferred form of this invention, would seem to deny access of the paramagnetic agent to all but the entrapped water, typically less than 0.1% of the total volume. Under such conditions, the NMR image would not be altered detectably by the presence of vesicle-encapsulated contrast agent. Only if water exchanges sufficiently rapidly across the bilayer is the relaxation rate of the bulk water enhanced, Andrasko et al, *NMR Study of Rapid Water Diffusion Across Lipid Bylayers in Dipalymitoyl Lecithin Vesicles*, Biochem. Biophys. Res. Comm., 1974, 60, p. 813–819. The present invention addresses this problem by providing a formulation of micelle and paramagnetic material that simultaneously maximizes micelle stability while permitting adequate rates of water exchange across the membrane.

Phospholipid vesicles are known to concentrate in certain tissues, so additional enhancement will come from tissue specificity. For example, phospholipid vesicles have been observed to accumulate in implanted tumors of mice, Proffitt et al, *Liposomal Blockade of the Reticuloendothelial System: Improved Tumor Imaging with Small Unilamella Vesicles*, Science, 1983 220 p. 502–505, Proffitt et al, *Tumor-Imaging Potential of Liposomes Loaded with In-111-NTA: Biodistribution in Mice*, Journal of Nuclear Medicine, 1983, 24, p. 45–51.

The invention also extends the use of micellular particles as contrast agent carriers to applications where the micelles are attached to antibodies. While it has been reported that a selective decrease in $T_1$ relaxation times of excised heart may be obtained using manganese-labeled monoclonal antimyosin antibody, Brady, et al, *Selective Decrease in the Relaxation Times of Infrared Myocardium with the Use of a Manganese-Labelled Monoclonal Antibody*, Soc. Magn. Res. Med., Works in Progress, Second Annual Meeting, 1983, p. 10, heretofore, due in large measure to considerations such as toxicity referred to above, the practical use of such antibodies has been significantly restricted. With the present invention, however, increased sensitivity is obtained and specificity is maintained by attachment of antibody to the surface of micellular particles. The antibodies provide high specificity for cell or tissue types, while the attached vesicle agent carriers amplify the NMR contrast enhancement over what can be achieved with ions bound to antibody alone.

SUMMARY OF THE INVENTION

The invention described herein is directed to preparations of micellular particles such as small unilamellar vesicles, with which a paramagnetic material is associated, typically paramagnetic compounds enclosed within the vesicles. The vesicles may or may not have antibodies, such as antimyosin, or antifibrin, attached to the surface or have other surface modifications for which there are specific cell receptors in certain tissue.

Examples of vesicle constituents are phospholipids such as distearoylphosphatidylcholine (DSPC), dipalmitoylphosphatidylcholine (DPPC), and dimyristoylphosphatidylcholine (DMPC). Examples of paramagnetic materials are salts of transition metals and the lanthanide and actinide series of the periodic table such as Gd(III), Mn(II), Cu(II), Cr(III), Fe(II), Fe(III), Co(II), Er(III), nickel(II) and complexes of such ions with diethylenetriaminepentaacetic acid (DTPA), ethylenediaminetetraacetic acid (EDTA) and other ligands. Other paramagnetic compounds include stable free radicals such as organic nitroxides.

Vesicle-encapsulated contrast agents may be prepared by forming the lipid vesicles in an aqueous medium containing the paramagnetic agent by any suitable means such as sonication, homogenization, chelate dialysis and the like, and then freeing the vesicles of external agent by ultrafiltration, gel filtration or similar method. Moreover, the internal solution of the paramagnetic material may be altered readily to maximize the relaxation rate per unit of agent as for example, by formulation with a charged polymeric material such as poly-L-Lysine.

DETAILED DESCRIPTION

Definitions and Abbreviations

As used herein, "micellular particle" and "micelles" refer to particles which result from aggregations of amphiphilic molecules. In this invention, preferred amphiphiles are biological lipids.

"Vesicle" refers to a micelle which is in a generally spherical form, often obtained from a lipid which forms a bilayered membrane and is referred to as a "liposome". Methods for forming these vesicles are, by now, very well known in the art. Typically, they are prepared from a phospholipid, for example, distearoyl phosphatidylcholine or lecithin, and may include other materials such as neutral lipids, and also surface modifiers such as positively or negatively charged compounds. Depending on the techniques for their preparation, the envelope may be a simple bilayered spherical shell (a unilamellar vesicle) or may have multiple layers within the envelope (multi-lamellar vesicles).

DSPC=distearyol phosphatidylcholine
Ch=cholestrol
DPPC=dipalmitoylphosphatidylcholine
DMPC=dimyristoylphosphatidylcholine
DTPA=diethylenetriaminepentaacetic acid
EDTA=ethylenediaminetetracetic acid
SUV=small unilamellar vesicles Materials and Preparation of Micelles Complexes of paramagnetic compounds were prepared in deionized water or in a buffer of 4.0 mM $Na_2HPO_4$, 0.9% (by weight) NaCl, pH 7.4 (PBS).

Gd(III)-citrate. A stock solution of 1.0 mM Gd(III)10.0 mM citrate was made by dissolving 10.0 $\mu$ moles $GdCl_3.6H_2$ (99.999%, Aldrich) in 9 ml deionized water and adding 100 moles $Na_3$citrate (analytical reagent, Mallinckrodt). The pH was adjusted to neutrality and the volume brough to 10.0 mL in a volumetric flask.

Mn(II)-citrate. A stock solution of 1.0 mM Mn (II)10.0 mM citrate was made by adding 10.0 $\mu$ moles $MnCl_2.4H20$ (Baker analyzed) and 100 $\mu$ moles sodium citrate to 9 ml water. The solution was neutralized and made up to 10.0 ml in a volumetric flask.

Gd(III)-DTPA. A stock solution of 200 mM Gd(III)-210 mM DTPA was made by dissolving 2.10 mmoles DTPA in minimum 6 N NaOH in a 10 ml volumetric flask. 2.0 mmoles GdC13.6H20 were added and the pH adjusted to 7.4 with 6 N NaOH, after which the sample was made up to 10.0 ml in the flask.

La(III)-DTPA. A stock solution of 200 mM La(III)-210 mM DTPA was made up in a manner analogous to the Gd(III)DTPA stock using $LaCl_3.7H_2O$ (99.999%, Aldrich).

Er(III)-EDTA. Stock solutions were prepared in a manner analogous to Gd(III)-DTPA.

Poly-L-lysine hydrobromide of approximate average molecular weights 25,000 and 4,000 were obtained from Sigma Chemical Co.

Cholesterol (98%) was from Mallinckrodt. DSPC was synthetic material from Cal-Biochem.

DSPC/cholesterol vesicle-encapsulated NMR contrast agent. 16 mg DSPC and 4 mg cholesterol were dissolved in 2 ml CHC13. 10 $\mu$ 1 of a solution of 0.16 mM cholesterol [u-14C] (56.5 mCi/mmole) in CHC13 were added for purposes of quantitating lipid concentrations in the final preparations. The lipid solution was evaporated to dryness in a vacuum dessicator and stored in the same, if not used immediately.

Small unilamellar vesicles (SUV) were formed in a solution of 200 mM Gd(III)-DTPA by adding 2.0 ml of the stock ion complex to the dried lipid tube. The mixture was complex to the dried lipid tube. The mixture was sonicated using an Ultrasonics, Inc. probe with a microtip at a power level of 56 W. The tube was cooled by partial immersion in a water bath, and $N_2$ was flowed over the sample during sonication. Total time of sonication was 15 min. or more until the solution was slightly opalescent.

Paramagnetic agent outside the vesicles was separated from the SUVs by passage through columns of Sephadex G-50 swollen in PBS, that had been loaded into 3 ml plastic syringe bodies and precentrifuged. The vesicle solution was placed at the top of the syringe and centrifuged with a glass tube positioned to collect the eluate. 300 $\mu$ 1 PBS was used to elute the vesicles from the columns. The procedure was repeated a total of 3 times to reduce the outside concentration of free agent and to exchange it for PBS.

Vesicle concentration in the final preparation was measured by counting an aliquot of the solution in the scintillation counter, using a standard cocktail. Average vesicle size was measured in a laser particle sizer Model 200 (Nicomp Instruments). The vesicle size was measured to be 600, ±100, A° in all experiments.

NMR Relaxation time measurements.

Unless otherwise indicated, measurements of $T_1$ and $T_2$ were made at 20 MHz with a pulsed NMR spectrometer (IBM PC/20) interfaced to a microcomputer (IBM PC). $T_1$ was measured by the inversion-recovery method (Farrar, T.C., Becker, E.D., *Pulse and Fourier Transform NMR*, 1971, Academic Press, New York.) and $T_2$ by the Carr-Purcell sequence (Carr, H.Y., Purcell, E.H., Effects of *Diffusion on Free Precession in NMR Experiments*, Phys. Rev., 1954, 94, p. 630–633.), as modified by Meiboom and Gill (Meiboom S., Gill D., *Modified Spin-Echo Method for Measuring Nuclear Relaxation Times*, Rev. Sci. Instrum., 1958, 29, p. 688–691.) Least-squares best fits of the data to single exponential recoveries were done automatically by the computer. Values of $T_1$ and $T_2$ reported are for a probe temperature of 38° C. $T_1$ values are estimated to have an experimental uncertainty of ±10% and a reproducibility of ±5%. $T_2$ values are generally accurate to within ±20% and reproducible to ±5%. This precision is sufficient clearly to demonstrate the effects claimed.

Some values of $T_1$ were measured with a Praxis II NMR spectrometer operating at 10 MHZ and a probe temperature of 25 C.

Animal Studies

EMT6 tumor tissue was transplanted subcutaneously into the flank of male Balb/c mice and allowed to grow for 10 days. On the 10th day, mice were injected i.v. with 200ul of vesicle solution or control buffer. Mice were sacrificed at intervals, and the tumors were dissected. In some experiments liver and spleen were also dissected. The tissue was rinsed in PBS, lightly blotted, weighed, and wrapped in air tight plastic bags. NMR relaxation measurements were made within ½ hr of dissection to limit water loss and consequent changes in $T_1$ and $T_2$.

DESCRIPTION OF DRAWINGS

Referring now in more detail to the figures of drawing, the improved results of the present invention will be discussed. In FIG. 1, relaxation rates of Er-EDTA and Mn citrate solutions are shown. Values of $1/T_1$ are plotted as a function of ion concentration at 10 MHz and 25C. The average value of $1/T_1$ for mouse soft tissue is indicated on the graph. The concentration scale for Er-EDTA is millimolar while that for Mn-citrate is micromolar. Addition of 18 mM Er-EDTA complex to a PBS solution increases $1/T_1$ to the mouse tissue value of 2.4 s-1. The same relaxation rate is achieved with only 0.17 mM Mn-citrate complex. The weak complex of Mn is 100 times more efficient for relaxation enhancement than the strongly complexed Er-EDTA, reflecting the intrinsically stronger relaxation power of the Mn(II) ion as well as the greater accessibility of the Mn to water.

In FIG. 2, the relaxation effects of Gd(III) are shown. At 20 MHz the addition of Gd-citrate to $H_2O$ increases $1/T_1$ to a value of 8.1 s-1 at 1.0 mM. When complexed to DTPA, the ion has one-half the relaxation effect. This reduction occurs because of displacement of water binding sites by the DTPA functional groups, partly balanced by an increased rotational correlation time of the complex. With the Gd-DTPA complex encapsulated in DSPC-cholesterol vesicles, the solution $1/T_1$ is still increased to a value of 2.5 s-1 for 1.0 mM total Gd-DTPA. While less efficient than free Gd-DTPA per unit ion, the vesicles still have a substantial effect on water relaxation.

Figure 3:
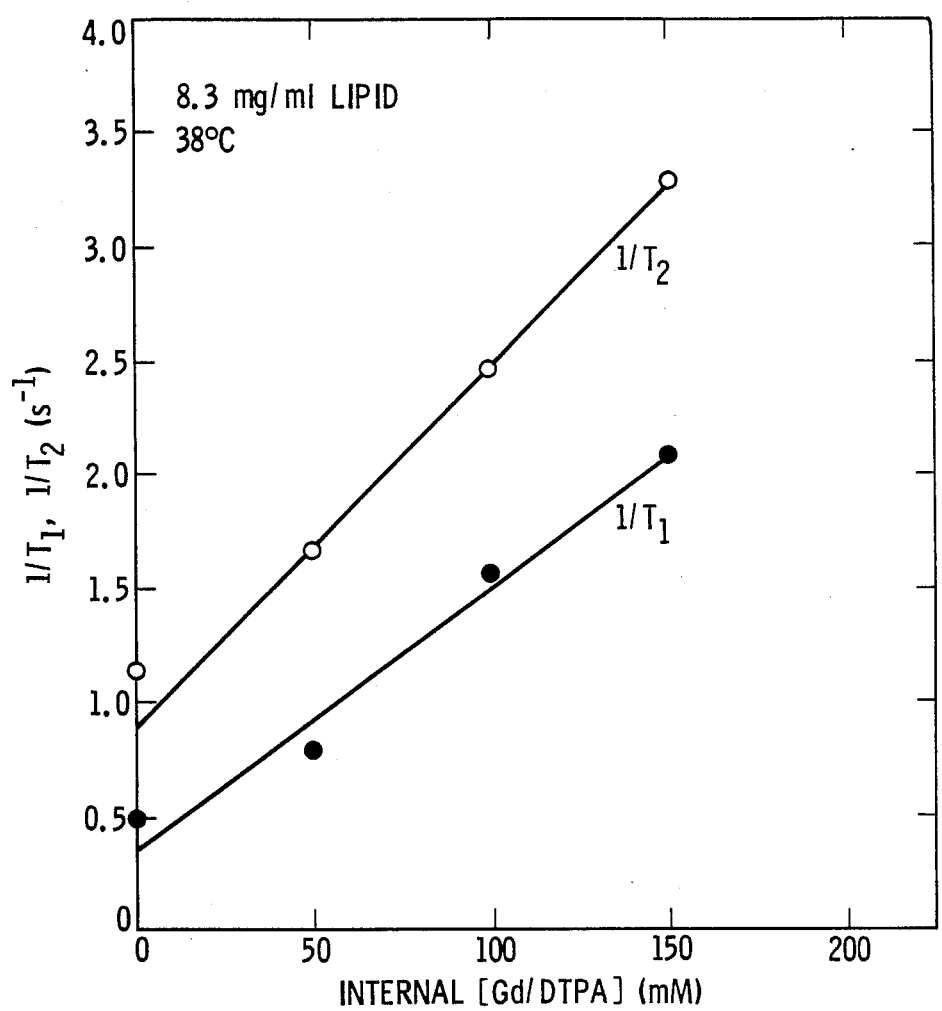
FIG. 3 illustrates internal paramagnetic ion complex concentration effects on $1/T_1$ and $1/T_2$. DSPC/cholesterol vesicles were prepared with increasing concentrations of Gd-DTPA in PBS encapsulated inside. The lipid (vesicle) concentrations were all adjusted with PBS to be equal at 8.3 mg/ml total lipid final concentration.

The effect of internal paramagnetic ion complex concentration on relaxation rates for vesicle-encapsulated Gd-DTPA is shown by FIG. 3. $1/T_1$ and $1/T_2$ for vesicle solutions increase linearly up to 150 mM internal Gd-DTPA concentration. Using the equation, $$\frac{1}{T_1} obsd = \frac{Pb}{(T_1b + 2b)} + \frac{1}{T_1a},$$

wherein b is for inside the vesicle and a is outside, $T_1b$ is the lifetime of water protons inside, $T_1b$ is the net relaxation time of water inside (made small by the paramagnetic agent), and Pb is the fraction of water inside the vesicle, predicts a linear dependence of $1/T_1$ on paramagnetic ion concentration until the value of $T_1$ becomes on the order of or less than $T_1b$. The results shown by FIG. 3 suggest that up to 150 mM Gd-DTPA concentration, $T_1$ inside the vesicles is greater than the exchange lifetime, $T_1b$.

Figure 4:
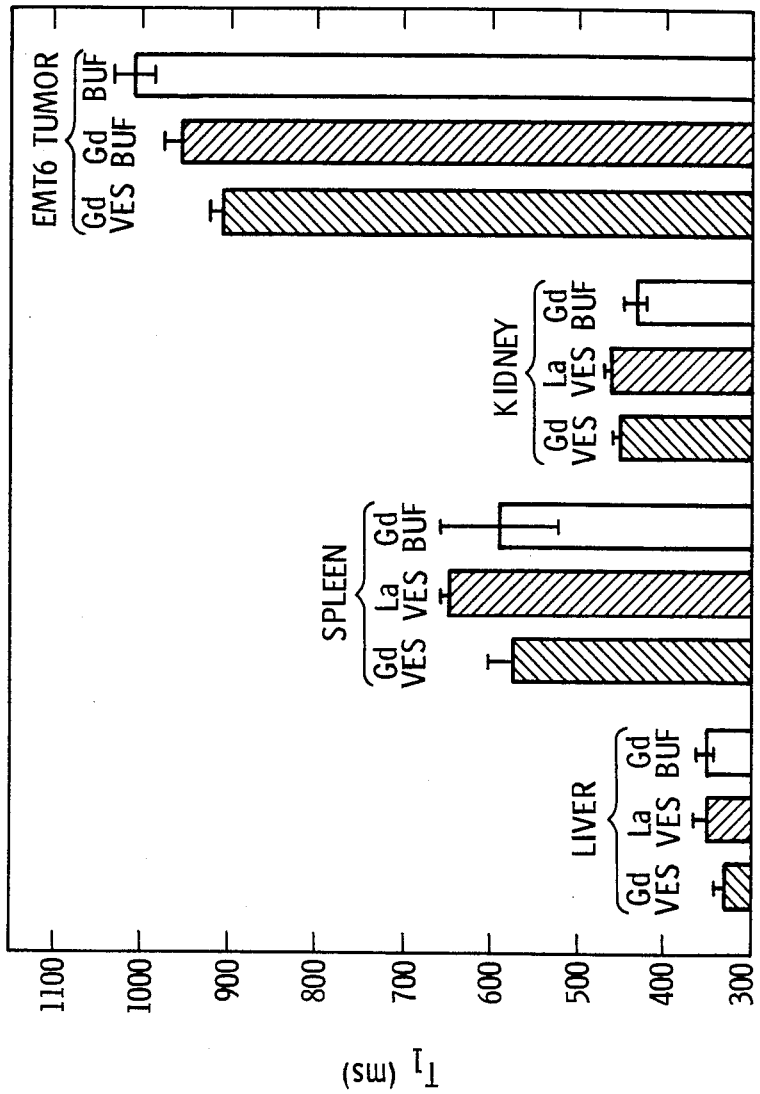
FIG. 4 illustrates relaxation rates of mouse tissue and tumors. Balb/c mice were injected with 200 $\mu$ 1 of 200 mM Gd-DTPA in DSPC/cholesterol vesicles (10 mg/ml lipid) (Gd Ves), 200 mM La-DTPA in DSPC/cholesterol vesicles (La Ves), 2.0 mM Gd-DTPA in PBS (Gd Buf) or PBS(Buf). After 16 hrs, the mice were sacrificed and the tissues dissected. Relaxation times are the average for at least 3 animals.

Relaxation effects on mouse tissue and tumors are illustrated in FIG. 4. The $T_1$ values of Balb/c mouse liver, spleen, kidney and EMT6 tumor tissue are compared 16 hrs after injection of paramagnetic agents or controls. Vesicle-encapsulated Gd-DTPA promotes a significant reduction in $T_1$ for spleen and for EMT6 tumors compared to the control of the diamagnetic lanthanide ion complex of La-DTPA in vesicles (spleen) or PBS buffer and PBS buffer plus 2.0 mM Gd/DTPA (tumor). In the case of Gd/DTPA-vesicle treated mice, the $T_1$ values averaged 17% less than controls without injected agent.

The foregoing data allow an estimate of the minimum Gd/DTPA or other paramagnetic species concentrations inside vesicles which provide contrast enhancement. There is a complex set of interrelating factors, such as proton exchange rate across membranes of the tumor cells, wash out rate of free Gd/DTPA from lipid vesicles, and altered rotational correlation time of the complex in a macromolecular environment, which contributes to the $T_1$ proton relaxation rate and subsequent contrast enhancement. The amount of accumulated vesicles in a particular tissue to be imaged dictates the minimum concentration of encapsulated paramagnetic material. For this Murine tumor model, it has been inferred that approximately 0.1% of the tumor volume is occupied by intact vesicles.

While the quantity of paramagnetic material to be encapsulated will vary, depending upon the specific material used as well as the factors mentioned above, in general, the paramagnetic material will be at least approximately 50 mM in the vesicles. The maximum quantity will be dictated by considerations of cost, toxicity and vesicle formulation, but ordinarily will not be above about 1 M encapsulated concentration.

Figure 5:
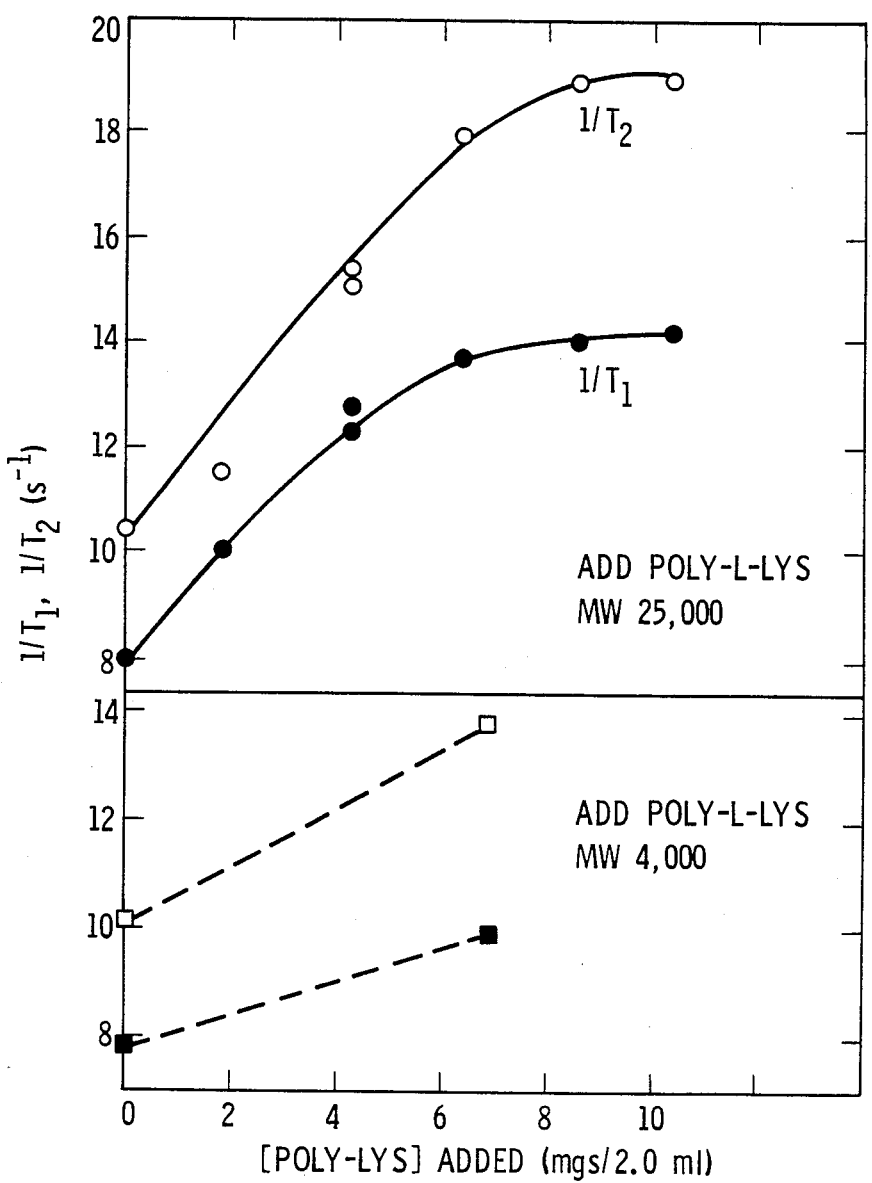
FIG. 5 shows the effect of added poly-L-lysine on relaxation rates of Gd-DTPA solutions. Dry weighed aliquots of poly-L-lysine were dissolved in 2.0 ml of 2.0 mM Gd-DTPA in $H_2O$. $T_1$ and $T_2$ were measured as described in the text.

FIG. 5 illustrates the enhanced relaxation rates through addition of a polymer. The relaxation effect of Gd-DTPA can be enhanced by the addition of the positively charged polymer, poly-L-lysine. FIG. 5 shows the result of adding poly-L-Lys of average MW 25,000 to a solution of 2.0 mM Gd-DTPA in H20. A 40% increase in relaxation rate $1/T_1$ is obtained and an 30% increase in $1/T_2$. The effect of added poly-L-lysine plateaus above 3 mg/ml showing a "weak binding" situation. This leveling off also shows that the increased relaxation rate is not due to an increase in viscosity, since the effect there would be linear in added poly-Lys over the whole concentration range. Smaller molecular weight poly-L-Lys is less effective on a weight basis. Gd-DTPA is a negatively charged complex which binds reversibly to the positive charge of the poly-Lys. The large size and consequent slow tumbling of the macromolecule made relaxation of the paramagnetic ion more efficient. This effect can be used by co-encapsulating Gd-DTPA and poly-Lys or some like positively charged macromolecule to increase the effect per unit ion of Gd and thus decrease net toxicity of the preparation.

Figure 6:
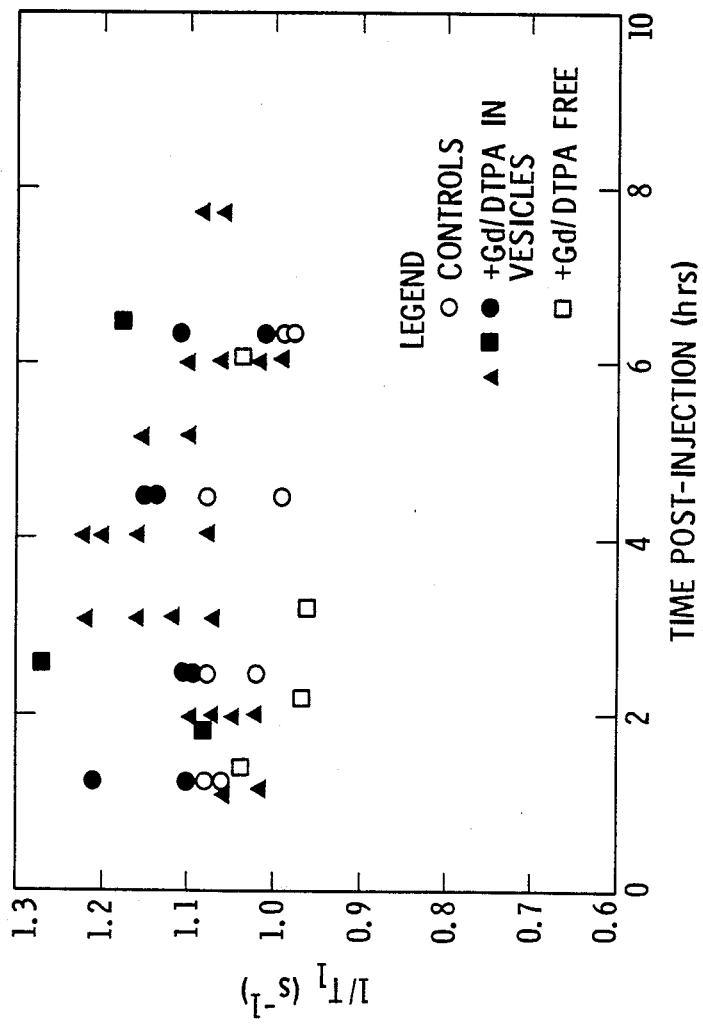
FIG. 6 illustrates the time course of $1/T_1$ for mouse tumors. Preparations of 10 mg/ml lipid vesicles containing 200 mM Gd-DTPA inside were injected (200 $\mu$ 1) into the tail vein of Balb/C mice having 10 day old EMT6 tumors from previous implants. The mice were sacrificed at intervals and $T_1$ of the tumors measured immediately after dissection. Controls were either no injection (O) or 200 $\mu$ 1 of 2.0 mM Gd-DTPA in PBS (☐). Three separate experiments are collected in this graph. For the ○ and ☐ data, the points each represent $T_1$ for a single tumor. For the Δ data, 2 or 3 $T_1$ values were occasionally measured for a single tumor.

Time course of relaxation effect on EMT6 tumors is shown in FIG. 6. The maximal effect of vesicle-encapsulated Gd-DTPA is achieved 3–4 hrs after injection of the agent. The average effect at 4 hrs is approximately equal to that at 16 hrs postinjection, suggesting that a steady-state condition obtains where the rate of uptake by tumor is matched by loss of agent to the circulation.

Three different liposome formulations were tested at doses higher than used for data of FIG. 6 for their relaxation effects on EMT6 tumors subcutaneously implanted in Balb/c mice. The mice were injected intravenously with the agent and then sacrificed at intervals. Tumor and liver $T_1$ values were measured within ½ hour of sacrifice of the animal. The results are set forth in Table I for tumors and in Table II for liver. Animals receiving only buffer had an average tumor $T_1$ value of $960\pm41$ ms (n=25) and an average liver $T_1$ value of $392\pm31$ ms (n=24). The tumor relaxation time decreased to $665\pm28$ ms (n=4) at 24 hours post injection for the 1:1 DSPC/CHOL formulation, while the livers of these animals had average $T_1$ values of $370\pm13$ ms (n=4). The $T_1$ change of 44% for the tumors is substantially larger than that for the liver (6%).

With many liposome formulations in common use, liver (and spleen) accumulate the largest fraction of the vesicle dose. The particular formulation of the present invention is thus far more specific for the tumor, at least in its effect on NMR relaxation times. The vesicle-encapsulated paramagnetic complex of the present invention accordingly fulfills the requirement of an NMR imaging contrast agent; that is, it leads to reduced values of $T_1$ in selected tissues. In this case, the original long $T_1$ of the tumor before contrast agent (average 960 ms) will leave the tumor dark in an NMR image, while, after injection of agent, the tumor would appear brighter in the scan.

TABLE I

TUMOR RELAXATION RATE
EMT6 Tumor in Flank of Balb/c Mouse
(10 day tumor growth)
Vesicle-encapsulated NMR Contrast Agent
Values are $T_1$ (in ms) ± standard deviation
n = number of mice

| Formulation* | Post-injection Time (hr) 1-2 | 2-5 | 5-8 | 24 | Notes |
|---|---|---|---|---|---|
| PBS Control | 962 ± 24  n = 9 | 974 ± 50  n = 11 | 920 ± 19  n = 4 | 926 | Global Average 960 ± 41  n = 25 |
| DPPC/CHOL 2:1 Gd/DTPA 200 mN | 869 ± 28  n = 14 | 840 ± 30  n = 13 | 845 ± 40  n = 13 | | |
| DSPC/CHOL 2:1 GD/DTPA 200 mMl | 812 ± 45  n = 8 | 768 ± 30  n = 8 | 769 ± 28  n = 4 | | |
| DSPC/CHOL 1:1 Gd/DTPA 200 mM | | 710 ± 19  n = 2 | 720 ± 21  n = 3 | 665 ± 28  n = 4 | |

*Injection volume = 250–300 ml Lipid concentration generally 20 mg/ml

TABLE II

LIVER RELAXATION RATE
Tumor bearing Balb/c Mouse
Post Contrast Agent Injection
Vesicle-encapsulated NMR Contrast Agent
Values are $T_1$ (in ms) ± standard deviation
n = number of mice

| Formulation* | Post-injection Time (hr) 1-2 | 2-5 | 5-8 | 24 | Notes |
|---|---|---|---|---|---|
| PBS Control | 400 ± 39  n = 8 | 380 ± 26  n = 12 | 411 ± 6  n = 3 | 412  n = 1 | Global Average 392 ± 31  n = 24 |
| DPPC/CHOL 2:1 Gd/DTPA 200 mN | 379 ± 35  n = 11 | 377 ± 29  n = 11 | 375 ± 34  n = 11 | | |

TABLE II-continued
LIVER RELAXATION RATE
Tumor bearing Balb/c Mouse
Post Contrast Agent Injection
Vesicle-encapsulated NMR Contrast Agent
Values are $T_1$ (in ms) ± standard deviation
n = number of mice

| Formulation* | Post-injection Time (hr) | | | | Notes |
|---|---|---|---|---|---|
| | 1-2 | 2-5 | 5-8 | 24 | |
| DSPC/CHOL 2:1 GD/DTPA 200 mMl | 349 ± 17 n = 11 | 345 ± 13 n = 11 | 379 ± 29 n = 7 | | |
| DSPC/CHOL 1:1 Gd/DTPA 200 mM | | 330 ± 32 n = 2 | 342 ± 11 n = 3 | 370 ± 13 n = 4 | |

*Injection volume = 250–300 ml Lipid concentration generally 20 mg/ml

Figure 1:
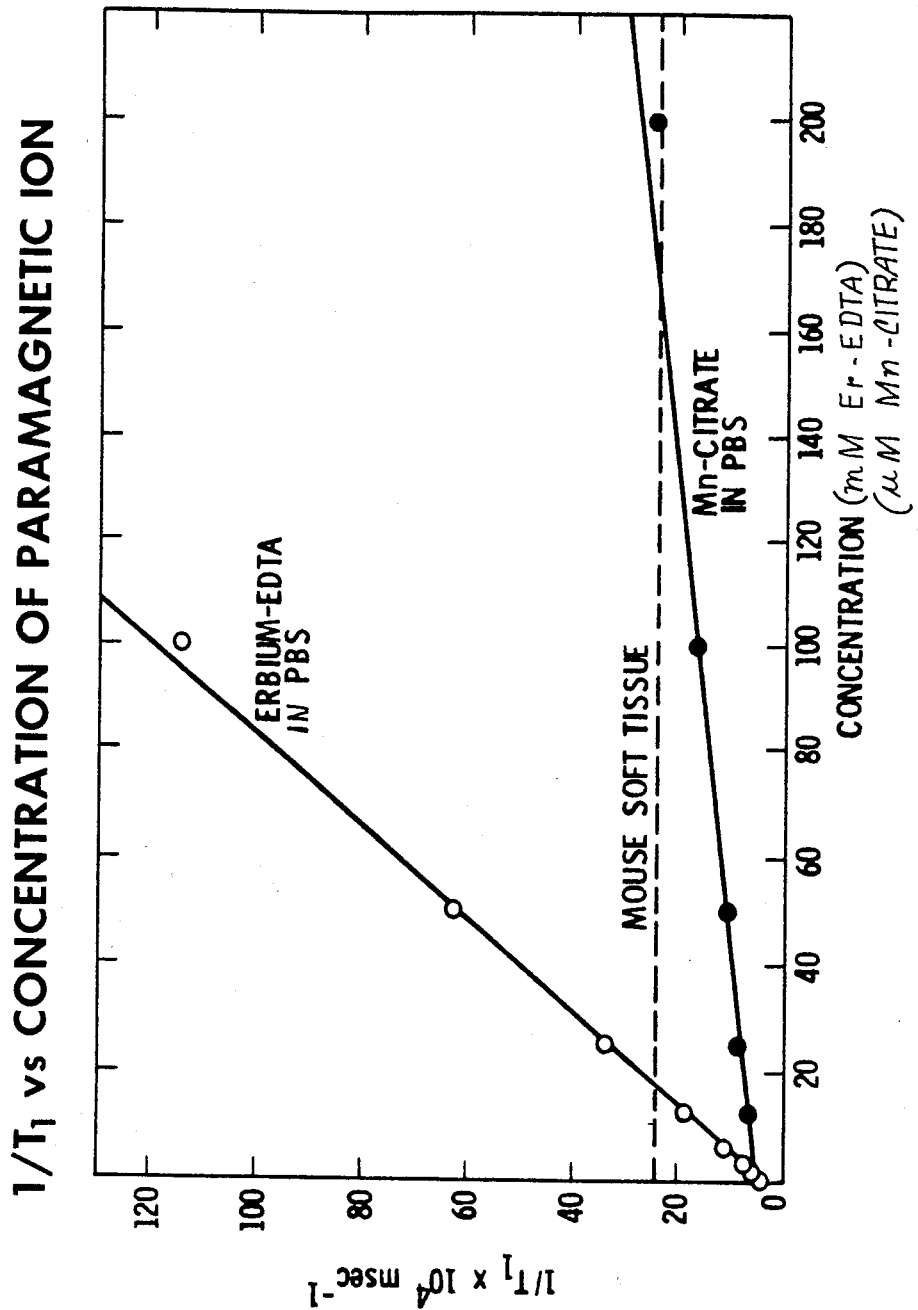
FIG. 1 is a plot of longitudinal relaxation rate as a function of added paramagnetic ion concentration. Aliquots of the stock solutions were added to PBS buffer. $T_1$ measurements were made at 10 MHz using the 90°-90° method. Probe temperature was 25°. Concentration scale for Er-EDTA is in mM units while for Mn-citrate the units are $\mu M$.
Figure 2:
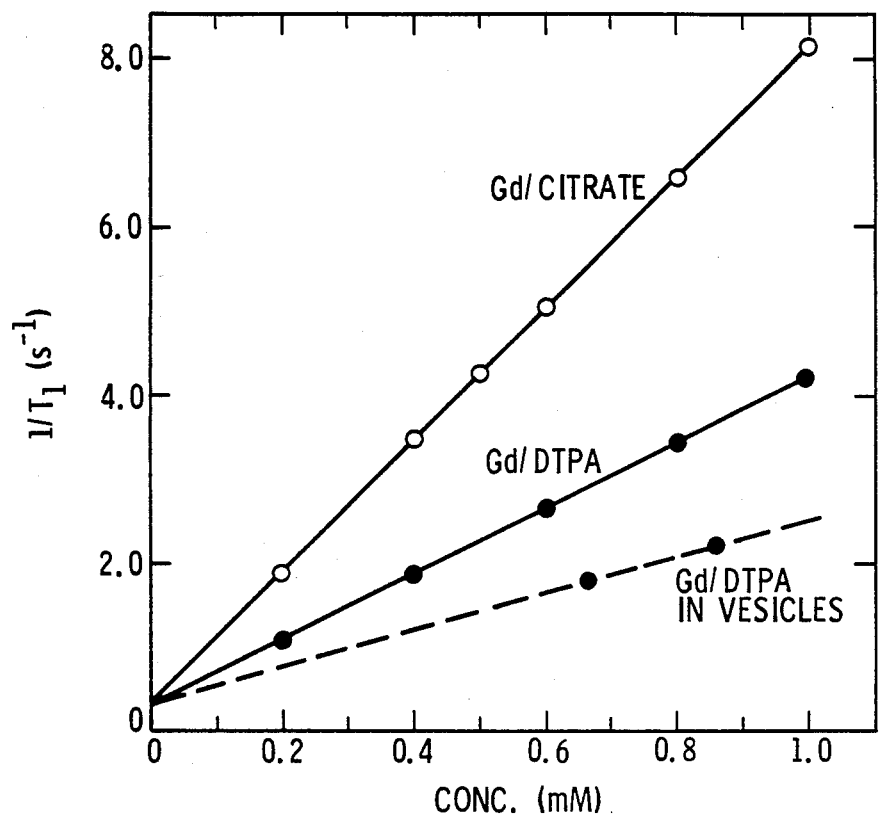
In FIG. 2, the dependence of $1/T_1$ on added Gd ion in various forms is illustrated. Aliquots of stock solutions were added to water (Gd/citrate) or PBS (Gd/DTPA and Gd/DTPA in vesicles) to give the total concentration of ion indicated.

For an NMR imaging contrast agent to be most useful, it must yield the maximum increase of $1/T_1$ possible with minimum toxicity, and have specificity for tissue type. The invention provides these features. A macromolecular assembly can increase the relaxation effect per unit ion, as demonstrated by the effect of added poly-Lys on $1/T_1$ and $1/T_2$ of Gd-DTPA solutions (FIG. 5). Low toxicity is gained by associating the normally toxic paramagnetic ion with a strong chelate in a macromolecular assembly (e.g. encapsulation in a vesicle) which keeps the ion out of circulation. NMR relaxation is enhanced by formulating the vesicle to maximize access of $H_2O$ protons to the ion. This was accomplished as shown by the strong relaxation effect of encapsulated Gd-DTPA (FIG. 2). Tissue specificity is provided by the complex nature of the micellular assembly for which biological recognition processes cause the macromolecule to distribute to certain sites. This is demonstrated for phospholipid vesicles by the differential influence on tissue relaxation rates (FIG. 4, tables I and II) and by the specific effect on tumor relaxation of Gd-DTPA encapsulated in vesicles versus approximately the same total concentration of Gd-DTPA free in solution (FIGS. 4 and 6).

It has been described herein that antibodies can be bound to vesicles to obtain tissue specificity, Martin et al, *Immunospecific Targeting of Liposomes to Cells,* Biochemistry, 1981, 20, p. 4229–4238, the disclosure of which is specifically incorporated herein by reference. Antimyosin has potential for NMR imaging of infarcted heart muscle. Moreover preparation of antifibrin has recently been reported; Hui et al, *Monoclonal Antibodies to a Synthetic Fibrin-Like Peptide Bind to Human Fibrin but not Fibrinogen,* Science, 1983, 222 p. 1129–1131. This antibody would be expected to concentrate at the sites of blood clots, where fibrin has been formed. Vesicle agent carriers attached to antifibrin could provide NMR contrast for imaging clots and thrombin in blood vessels. There are, however, other surface modifications which provide for cell recognition that are known to alter the biodistribution of the vesicles. For example, carbohydrate receptor analogues bound to the vesicle surface have been shown to target vesicles. (Mauk, et al., Targeting of Lipid Vesicles: Specificity of Carbohydrate Receptor Analogues for Leukocytes in Mice, Proc. Nat'l. Acad. Sci. USA 77, 4430–4434 (1980); Mauk, et al., Vesicle Targeting: Timed Release for Leukocytes in Mice by Subcutaneous Injection, Science 207, 309–311 (1980).) Such targeting by surface modifications are directly applicable for altering the biodistribution of paramagnetic ion.

What is claimed is:

1. Magnetic resonance imaging contrast agents for scanning tissue comprising bilayer vesicles with paramagnetic material encapsulated therein, said vesicles formulated with an agent to promote vesicle stability for a sufficient time to allow biodistribution of said vesicles for scanning of said tissue and formulated to permit adequate water proton exchange across the vesicle bilayer to provide contrast for scanning said tissue.

2. The contrast agents of claim 1 in which said micellular particles are vesicles.

3. The contrast agents of claim 2 in which said vesicles are formulated with an agent to promote vesicle stability and water exchange across the vesicle bilayer.

4. The contrast agents of claim 3 in which said vesicles are formulated with cholestrol.

5. The contrast agents of claims 1, 2, 3 or 4 in which antibodies, carbohydrates, or other cell recognition targeting agents are attached to said micellular particles, to provide specific targeting.

6. The contrast agents of claim 5 in which said targeting agent is the antibody antimyosin.

7. The contrast agents of claim 5 in which said targeting agent is the antibody antifibrin.

8. The contrast agents of claims 1, 2 or 3 in which said paramagnetic material is a salt of a transition metal or the lanthanide or actinide series of the Periodic Table.

9. The contrast agents of claim 7 in which said paramagnetic material is a salt of a paramagnetic ion selected from manganese, copper, gadolinum, erbium, chromium, iron, cobalt and nickel.

10. The contrast agents of claims 1, 2 or 3 in which said paramagnetic material is a paramagnetic compound including a stable free radical.

11. The contrast agents of claims 1, 2 or 3 which said paramagnetic material is a paramagnetic compound of a paramagnetic ion and a chelate.

12. The contrast agents of claims 1, 2, or 3 in which said paramagnetic material is present in a concentration of at least approximately 50 mM.

13. The contrast agents of claims 1, 2 or 3 in which said paramagnetic material is present in a concentration of from about 50 mM to approximately 1 M.

14. The contrast agents of claim 10 in which the efficiency of said paramagnetic material is enhanced by the addition of a charged polymer thereto.

15. The contrast agents of claim 11 in which said charged polymer is poly-L-lysine.

16. Magnetic resonance imaging contrast agents for scanning tissue comprising phospholipid bilayer esicles with paramagnetic material encapsulated therein, said paramagnetic material being a paramagnetic ion associated with a chelate and said vehicles formulated with an agent to promote vesicle stability for a sufficient time to allow biodistribution of said vesicles for scanning of said tissue and formulated to permit adequate water proton exchange across the vesicle bilayer to provide contrast for scanning of said tissue.

17. The contrast agents of claim 13 in which said vesicles are formulated with cholestrol.

18. The contrast agents of claim 14 in which said paramagnetic material is Gd-DTPA.

19. The contrast agents of claims 18 in which said paramagnetic material is present in a concentration of at least approximately 50 mM.

20. The contrast agents of claim 19 in which said paramagnetic material is present in a concentration of from about 50 mM to approximately 1 M.

21. Magnetic resonance imaging contrast agents for scanning tissue comprising bilayer vesicles having a paramagnetic material associated therewith, said vesicles formulated with an agent to promote vesicle stability for a sufficient time to allow biodistribution of said vesicles for scanning of said tissue and formulated to permit adequate water proton exchange across the vesicle bilayer to provide contrast for scanning of said tissue.

22. The contrast agents of claim 21 in which said paramagnetic material is associated with a chelating agent bound to the surface of said micellular particles.

23. The contrast agents of claim 1 wherein said tissue is tumor tissue.

24. The contrast agents of claim 16 wherein said tissue is tumor tissue.

25. The contrast agents of claim 21 wherein said tissue is tumor tissue.

* * * * *

UNITED STATES PATENT AND TRADEMARK OFFICE
CERTIFICATE OF CORRECTION

PATENT NO. : 4,728,575

DATED : March 1, 1988

INVENTOR(S) : Gamble et al.

It is certified that error appears in the above-identified patent and that said Letters Patent is hereby corrected as shown below:

In the abstract, change "cholestrol" to -- cholesterol --.

Column 1, line 63, change "affecting" to -- effecting --.

Column 2, line 33, change "Unilamella" to -- Unilamellar --.

Column 3, line 8, change "ethylenediamimetetraacetic" to -- ethylenediaminetetraacetic --; line 14, change "chelate" to -- cholate --; line 43, change "distearyol" to -- distearoyl --; line 44, change "cholestrol" to -- cholesterol --; line 48, change "ethylenediaminetetracetic" to -- ethylenediaminetetraacetic --; line 56, change "$GdCl_3.6H_2$" to -- $GdCl_3.6H_2O$ --; line 57, change "moles" to -- $\mu$moles --; line 59, change "brough" to -- brought --; line 62, change "$MnCl_2 \cdot 4H2O$" to -- $MnCl_2 \cdot 4H_2O$ --; and line 68, change "$GdCl3.6H2O$" to -- $GdCl_3 \cdot 6H_2O$ --.

Column 4, lines 16 and 17, change "CHC13" to -- $CHCl_3$ --; lines 24-25, delete "The mixture was complex to the dried lipid tube."; line 47, delete "," after -- 600 -- and after -- 100 --.

Column 5, lines 3 and 67, change "25C" to -- 25°C --; line , change "200 ul" to -- 200$\mu$l --.

Column 6, line 5, change "mM" to -- $\mu$M --; line 12, change "H?2O" to -- $H_2O$ --; lines 4, 13 and 20, change "s-1" to -- $s^{-1}$ --; lines 30-33, that portion of the equation reading "$\frac{Pb}{(T_1b+2b)}$" should read -- $\frac{Pb}{(T_1b+\tau_b)}$ --;

lines 34, 40 and 43, change "$T_1b$" to -- $\tau_b$ --; line 39, change "$T_1$" to -- $T_1b$ --.

UNITED STATES PATENT AND TRADEMARK OFFICE
CERTIFICATE OF CORRECTION

PATENT NO. : 4,728,575

DATED : March 1, 1988

INVENTOR(S) : Gamble et al.

It is certified that error appears in the above-identified patent and that said Letters Patent is hereby corrected as shown below:

Column 7, line 16, change "H2O" to -- $H_2O$ --.

In Tables I and II, the units following Gd/DTPA should read, mM in all instances; and "GD/DTPA" should read -- Gd/DTPA --.

Cancel Claims 2 and 3.

Claim 4, line 27, change "Claim 3" to -- Claim 1 --; line 28, change "cholestrol" to -- cholesterol --.

Claim 5, line 29, delete ", 2, 3"; lines 31-32, change "micellular particles" to -- vesicles --.

Claims 8, 10, 11, 12, 13, change "claims 1, 2 or 3" to -- claim 1 --.

Claim 9, line 40, change "claim 7" to -- claim 8 --.

Claim 14, line 56, change "claim 10" to -- claim 11 --.

Claim 15, line 59, change "claim 11" to -- claim 14 --.

Claim 16, line 62, change "esicles" to -- vesicles --; line 65, change "vehicles" to -- vesicles --.

Claim 17, line 3, change "claim 13" to -- claim 16 --; line 4, change "cholestrol" to -- cholesterol --.

UNITED STATES PATENT AND TRADEMARK OFFICE
CERTIFICATE OF CORRECTION

PATENT NO. : 4,728,575

DATED : March 1, 1988

INVENTOR(S) : Gamble et al.

It is certified that error appears in the above-identified patent and that said Letters Patent is hereby corrected as shown below:

Claim 18, line 5, change "claim 14" to -- claim 16 --.

Claim 19, line 7, change "claims 18" to -- claim 16 --.

Claim 20, line 10, change "claim 19" to -- claim 16 --.

Claim 22, line 9, change "micellular particles" to -- vesicles --.

Signed and Sealed this

Nineteenth Day of September, 1989

Attest:

DONALD J. QUIGG

Attesting Officer

Commissioner of Patents and Trademarks